United States Patent
Bennani

(12) 
(10) Patent No.: US 6,521,790 B2
(45) Date of Patent: Feb. 18, 2003

(54) ALKYNYL AMIDES AND THEIR THERAPEUTIC APPLICATIONS

(75) Inventor: Youssef L. Bennani, Beachwood, OH (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 10/004,482

(22) Filed: Nov. 1, 2001

(65) Prior Publication Data

US 2002/0123528 A1 Sep. 5, 2002

Related U.S. Application Data

(60) Provisional application No. 60/244,950, filed on Nov. 1, 2000.

(51) Int. Cl.$^7$ .................. C07C 233/05; A61K 31/16
(52) U.S. Cl. .................. 564/159; 564/204; 514/616; 514/627
(58) Field of Search .................. 564/159, 204; 514/616, 627

(56) References Cited

U.S. PATENT DOCUMENTS

5,786,380 A    7/1998   Nau et al. .................. 514/557

FOREIGN PATENT DOCUMENTS

WO    95 01956    1/1995

OTHER PUBLICATIONS

Jacobi et al, J. Org. Chem. 1996, vol. 61, pp 5013–5023.*
Jacobi et al, Tetrahedron Lett., 1995, vol. 36, No. 8, pp 1193–1196.*
Jacobi et al, J. Am. Chem. Soc., 1999, 121, pp 1958–1959.*
Berge, S.M. et., "Pharmaceutical Salts," J. Pharmaceutical Sciences 66:1–19 (1977).
Cereghino, J.J. et al., "Introduction to Antieplieptic Drugs" Antiepileptic Drugs 4$^{th}$ edition, p. 1–11 (1995).
Chen, G. et al., "The mood–stabilizing Agents Lithium and Valproate Robustly Increase the Levels of the Neuroprotective Protein bcl–2 in the CNS," Journal of Neurochemistry 72(2):879–882(1999).
Danek, A. et al., Restless Legs Syndrome, Neurological Disorders: Course and Treatment 819–823 (1996).
Evans, D.A. et al., "Asymmetric Alkylation Reactions of Chiral Imide Enolates. A Practical Approach to the Enantioselective Synthesis of alpha–substituted Carboxylic Acid Derivatives," J. Am. Chem. Soc. 104:1737–1739 (1982).
Hering, R. et al., "Sodium valproated in the treatment of cluster headache: an open clinical trial," Cephalalgia 9:195–198 (1989).
Hering, R. et al., "Sodium valproate in the prophylactic treatment of migraine: a double–blind study versus placebo," Cephalagia 12:81–84 (1992).
ICPAC Commission on Nomenclature of Organic Chemistry 45:13–30 (1976).
Jacobi, P. A. et al., Studies on corrin Synthesis. A solution to the Introduction of Meso Substituents, J. Org. Chem. 64:1778–1779 (1999).
Jacobi, P.A. et al., "Iterative Synthesis of Semicorrins, Tripyrroline, and Higher Analogues," J. Am. Chem. Soc. 121:1958–1959 (1999).
Jacobi, P.A. et al., "Synthesis of Cyclic Enamides by Intramoleclar Cyclization of Acetylenic Amides," Tetrahedron Letters 36(8):1193–1196 (1995).
Jacobi, P.A. et al., "Toward the Synthesis of Biologically Important Chlorins, Isobacteriochlorins, and Corrins, Cyclic Enamides from Acetylenic Amides," J. Org. Chem. 61:5013–5023 (1996).
Jensen, R., "Sodium valproate has a prophylactic effect in migraine without aura: A triple–blind, placebo–controlled crossover study," Neurology 44:647–651 (1994).
Jurima–Romet, M. et al., "Cytotoxicity of unsaturated metabolites of balproic acid and protection by vitamins c and e in glutathione–depleted rat hepatocytes," Toxicology 112:69–85 (1996).
Mathew, N.T. et al., "Valproate in the treatment of persistent chronic daily headache. An open label study." Headache 31:71–74 (1991).
Mellich, G.A. et al., "Successful Treatment of Restless Leg Syndrome with Gabepentin," Neurology 45(suppl 4):A285–A286 (1995).
O'Keeffe, S.T., "Restless Legs Syndrome," Archives of Internal Medicine 156:243–248 (1996).
Post, R.M. et al., "Alternatives to Lithium for bipolar Affective Illness," Review of Psychiatry 9:170–202 (1990).
Post, R.M. et al., "Shared mechanisms in affective illness, epilepsy, and migraine," Neurology 44(suppl 7):S37–S47 (1994).
Prescott, "Methods in Cell Biology," Academic Press, New York 14:33 et seq (1976).

(List continued on next page.)

Primary Examiner—Shailendra Kumar
(74) Attorney, Agent, or Firm—Paul D. Yasger

(57) ABSTRACT

Compounds of formula (I)

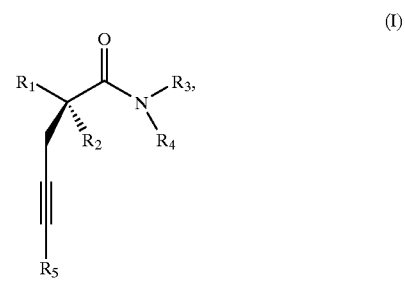

are novel and useful for treating seizure, migraine and psychiatric disorders.

28 Claims, No Drawings

OTHER PUBLICATIONS

Sachdev, P. et al., "Restlessness: the anatomy of a neuropsychiatric symptom," Austral New Zealand J. Psychiatry 30:38–53 (1996).

Swendlow, M., "Antioconvulsant Drugs and Chronic Pain," Clinical Neuropharmacology 7(1) :52–82 (1984).

Tang, W. et al., "Fluorinated Analogues as Mechanistic Probes in Valproic Acid Hepatotoxicity: Hepatic Microvesicular Steatosis and Glutathione Status," Chem. Res. Toxicol. 8(5) :671–682 (1995).

Tang, W. et al., "A comparative investigation of 2–propyl–4–pentenoic acid (4–ene vpa) and its alpha–fluorinated analogue: phase II metabolism and pharmacokinetics," Drug Metabolism and Disposition 25(2):219–227 (1997).

Tang, W. et al., "Time course of alpha–Fluorinated valproic acid in mouse brain and serum and its effect on synaptosomal γ–aminobutyric acid levels in comparison to valproic acid," J. Pharmacol. Exp. Ther. 282:1163–1172 (1997).

Chemical Abstracts, vol. 80, No. 15, Apr. 15, 1974, Columbus, OH, abstract No. 81951n.

Elmazar, et al., "Anticonsulsant and Neurotoxic Activities of Twelve Analogues of Valproic Acid", Journal of Pharmaceutical Scinences, vol. 82. No. 12, pp. 1255–1258 (1993).

* cited by examiner

ALKYNYL AMIDES AND THEIR THERAPEUTIC APPLICATIONS

This application claims priority to U.S. Provisional application Ser. No. 60/244,950, filed Nov. 1, 2000.

TECHNICAL FIELD

The present invention relates to alkynyl amides, to the use of these compounds to treat seizures, migraine, and psychiatric disorders, and to the preparation of these compounds.

BACKGROUND OF THE INVENTION

Epilepsy affects roughly 1% of the world's population. Among the drugs employed for control of epileptic seizures is valproic acid. Valproic acid (also referred to as VPA, valproate, di-n-propylacetic acid, DPA, 2-propylvaleric acid or 2-propylpentanoic acid) is an effective anticonvulsant.

Migraine is defined as a periodically occurring vascular headache characterized by pain in the head (usually unilateral), nausea and vomiting, photophobia, phonophobia, vertigo and general weakness. Migraine is the most common type of vascular headache and affects as much as 15% of the world's population. Of the different types of migraines, classical migraine and common migraine are the two most prevalent. The major difference between the two types of migraines is that classical migraines are preceded by the appearance of neurological symptoms before an attack whereas common migraines are not preceded by such symptoms. Migraine is caused by intermittent brain dysfunction. However, the precise pathophysiological mechanisms involved are not understood. The head pain is believed to involve blood vessel dilation.

Analgesics are often used to treat infrequent and mild migraines. Analgesics reduce the pain of a migraine and, in the case of aspirin, also discourage platelet aggregation. However, for moderate to severe migraines, stronger medications such as ergotamine and valproic acid are often necessary. Ergotamine tartrate is a vasoconstrictor which counteracts the painful dilation stage of the headache. When taken during the early stages of an attack, ergotamine tartrate helps to relieve the classic and common migraine symptoms. Valproic acid has been shown to be effective in prevention of migraine, however, its mechanism of anti-migraine action is unclear. It is believed that valproic acid increases brain gamma-aminobutyric acid (GABA) levels and in doing so may activate the GABA receptor and suppresses migraine-related events.

A number of psychiatric disorders may be treated with valproic acid, see: Loscher W., ed. Valproate, Basel Switzerland: Birkhauser Verlag, 1999; Post R. M., In Tasman A., Goldfinger, S. M., Kaufmann, C. A., eds. Review of psychiatry, volume 9, Washington D.C.: American Psychiatric Press, 1990, 170–202; and Jensen R., Brinck T., Olesen J., Neurology 44, 1994, 647. Such psychiatric disorders include: i) Mood Disorders; ii) Anxiety Disorders; iii) Attention-Deficit and Disruptive Behavior Disorders; iv) Behavioral Disturbances associated with dementia; v) Behavioral Disturbances associated with autism; vi) Schizophrenia; vii) Impulse Control Disorders; viii) Personality Disorders; and ix) Substance-related Disorders.

Mood Disorders include, but are not limited to, Depressive Disorders and Bipolar Disorders such as Manic episodes and Mixed episodes. Symptoms associated with Mood Disorders include, but are not limited to, depression, elevated, expansive or irritable mood, insomnia/hypersomnia, agitation and distractability or impulsivity.

Anxiety Disorders include, but are not limited to, Panic Disorder, Posttraumatic Stress Disorder and Generalized Anxiety Disorder. Symptoms associated with Anxiety Disorders include, but are not limited to, anxious mood, panic attacks, irritability, outbursts of anger and exaggerated startle response.

Attention-Deficit and Disruptive Behavior Disorders include, but are not limited to, Attention-Deficit/Hyperactivity Disorder Hyperactive-Impulsive Type, Conduct Disorder, Oppositional Defiant Disorder and Disruptive Behavior Disorder. Symptoms associated with Attention-Deficit and Disruptive Behavior Disorders include, but are not limited to, impulsivity, aggression, anger and loss of temper.

Symptoms associated with Behavioral Disturbances for both dementia and autism include, but are not limited to, verbal and physical agitation and aggression.

Symptoms associated with Substance-related Disorders, include but are not limited to, withdrawal and dependence.

Symptoms associated with schizophrenia, include but are not limited to, positive symptoms, negative symptoms and agitation.

Impulse Control Disorders include, but are not limited to, Intermittent Explosive Disorder. Symptoms associated with Impulse Control Disorders, include but are not limited to, verbal or physical aggressive impulses.

Personality Disorders include, but are not limited to, Borderline Personality Disorder. Symptoms associated with Personality Disorders, include but are not limited to, mood lability, irritability, agitation and aggression.

The symptoms listed for these psychiatric disorders are not an exhaustive description of the diagnostic category or disorder, but merely reflect some of the symptoms that may improve when treated with valproic acid. For Example, valproic acid may be used to treat general agitation or aggression not necessarily associated with any particular psychiatric-disorder.

Further, excitatory neurotransmitters such as glutamate and aspartate, as well as a variety of voltage-gated ion channels, are thought to play a central role in mediating cell death after a variety of cerebral insults including, but not limited to, ischemia, trauma, seizure and hypoglycemia. Many studies have shown that compounds or therapeutic strategies that decrease excitatory neurotransmission, for example, glutamate antagonists, ion channel blockers, anticonvulsants, and the like, elicit a neuroprotective effect in animal models of cerebral insults.

Recently, VPA has been shown to increase the levels of the neuroprotective protein B cell lymphoma protein-2 (bcl-2) in frontal cortex, findings that may have implications for the long-term treatment of various neurodegenerative disorders (Chen G., et al, Journal of Neurochemistry, 1999, 879–882).

Neuropathic pain affects a significant number of patients suffering from disorders of the brain or spinal cord, such as stroke, trauma, multiple sclerosis, and diabetes. Several known anticonvulsant compounds are efficacious in various analgesia models relevant to identifying therapeutic candidates for treating neuropathic pain (Lloyd and Morselli, in Psychopharmacology: The Third Generation of Progress, Raven Press, 1987). The use of anticonvulsants like valproate to treat various pain states has been documented extensively (Swendlow, J. Clin. Neuropharmacol., 7, 1984, 51–82).

Restlessness syndrome denotes a somatic (non-mental) restlessness characterized by involuntary movement of the limbs, as well as by a sense of physical (rather than mental) agitation, which is independent of mood and, hence, is distinguished from restlessness per se, see (Sachdev et al., Austral. New Zealand J. Psychiatry 30, 1996, 38–53.

The genus of restlessness syndromes, inclusive of numerous indications, can be observed in association with many organic and non-organic psychiatric illnesses. For example, drug-induced restlessness (tardive, chronic, and withdrawal akathisias), such as drug-induced extrapyramidal symptoms, is one of the most common side effects of neuroleptic, drug therapy. Also within the restlessness syndrome rubric are the so-called "restless leg syndrome" and "sleep-related periodic leg movements," pathologies that can be associated with head and/or spinal cord trauma and with lesions of the spinal cord. Idiopathic restless leg syndrome follows an autosomal dominant inheritance, with a variable clinical expression of symptoms.

Diminished GABAergic neurotransmission is implicated in the neurochemical basis of restlessness syndromes. Consistent with this notion, for instance, is the efficacy of drugs such as baclofen, valproate, gabapentin and the benzodiazepines, in the treatment of restless leg syndrome, an important indication, see (O'Keefe, Arch. Intem. Med. 156, 1996, 24348; Danek et al., in Neurological Disorders: Course and Treatment, pages 819–23, Academic Press, 1996; and Mellick and Mellick, Neurology 45(suppl), 1995, 285–86).

A relationship has been reported between epilepsy, migraine and psychiatric disorders (Post and Silberstein, Neurology, 1994, 44(suppl 7), S37–S47). Although the three disorders are distinct, they all are paroxysmal dysregulations of the nervous system that partially overlap in their pharmacology. Some drugs, such as valproic acid, are effective in treating all three syndromes, see: (Post R. M., In Tasman A., Goldfinger, S. M., Kaufmann, C. A., eds. Review of psychiatry, volume 9, Washington D.C.: American Psychiatric Press, 1990, 170–202; and Jensen R., Brinck T., Olesen J., Neurology 44, 1994, 647), suggesting the presence of shared underlying pathophysiology, while other drugs are effective for treating one syndrome. For example, β-adrenergic adrenoreceptor blockers which are effective against migraine are not useful for treating the other two syndromes and may even exasperate depression.

There has been considerable effort to discover analogs of valproic acid that are equally effective. One study has demonstrated that the valproic acid analog 2-propyl-4-hexynoic acid is an effective antiepileptic with a longer duration of activity.

Alpha-fluorinated valproic acid, 2-fluoro-2-propylpentanoic acid, has also been reported (Ph.D. thesis of Wei Tang, University of British Columbia, 1996; W. Tang et al., Chem. Res. Toxicol. (1995), 8(5), 671–682; M. Jurima-Romet et al., Toxicology (1996), 112(1), 69–85; W. Tang and F. Abbott, Drug Metab. Dispos. (1997), 25(2), 219–227). The anticonvulsant activity and pharmacokinetics of this compound were studied, and its pharmaceutical potential was speculated upon (F. Abbott, W. Tang, J. Palaty, J. Pharmacol. Exp. Ther. (1997), 282, 1163–1172). The compound was reported to be less potent than VPA, and the hepatotoxic, sedative, or teratogenic properties were not disclosed.

SUMMARY OF THE INVENTION

In its principle embodiment, the present invention discloses compounds of formula (I):

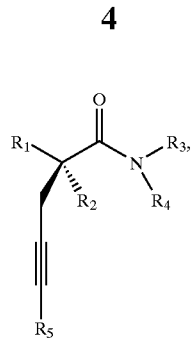

wherein
- $R_1$ is selected from the group consisting of alkyl and haloalkyl;
- $R_2$ is selected from the group consisting of hydrogen, alkyl and fluorine;
- $R_3$ is selected from the group consisting of hydrogen, alkyl and $(NR_AR_B)$carbonylalkyl wherein $R_A$ and $R_B$ are each independently selected from the group consisting of hydrogen and alkyl;
- $R_4$ is selected from the group consisting of hydrogen and alkyl; and
- $R_5$ is selected from the group consisting of hydrogen and alkyl.

DETAILED DESCRIPTION OF THE INVENTION

All patents, patent applications, and literature references cited in the specification are herein incorporated by reference in their entirety. In the case of inconsistencies, the present disclosure, including definitions, will prevail.

In its principle embodiment, the present invention discloses compounds of formula (I):

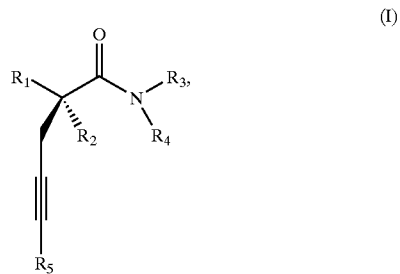

wherein
- $R_1$ is selected from the group consisting of alkyl and haloalkyl;
- $R_2$ is selected from the group consisting of hydrogen, alkyl and fluorine;
- $R_3$ is selected from the group consisting of hydrogen, alkyl and $(NR_AR_B)$carbonylalkyl wherein $R_A$ and $R_B$ are each independently selected from the group consisting of hydrogen and alkyl;
- $R_4$ is selected from the group consisting of hydrogen and alkyl; and
- $R_5$ is selected from the group consisting of hydrogen and alkyl.

In a preferred embodiment, compounds of the present invention have formula (I) wherein $R_2$ is hydrogen; $R_1$, $R_3$, $R_4$ and $R_5$ are as defined in formula (I).

In another preferred embodiment, compounds of the present invention have formula (I) wherein $R_2$ is alkyl; $R_1$, $R_3$, $R_4$ and $R_5$ are as defined in formula (I).

In another preferred embodiment, compounds of the present invention have formula (I) wherein $R_2$ is fluorine; $R_1$, $R_3$, $R_4$ and $R_5$ are as defined in formula (I).

In another preferred embodiment, compounds of the present invention have formula (I) wherein $R_1$ is propyl; $R_5$ is methyl; and $R_2$, $R_3$ and $R_4$ are as defined in formula (I).

In another preferred embodiment, compounds of the present invention have formula (I) wherein $R_1$ is propyl; $R_3$ is hydrogen; $R_5$ is methyl; and $R_2$ and $R_4$ are as defined in formula (I).

In another preferred embodiment, compounds of the present invention have formula (I) wherein $R_1$ is propyl; $R_3$ is $(NR_AR_B)$carbonylalkyl; $R_5$ is methyl; and $R_2$ and $R_4$ are as defined in formula (I).

In another preferred embodiment, compounds of the present invention have formula (I) wherein $R_1$ is propyl; $R_2$ is hydrogen; $R_3$ is $(NR_AR_B)$carbonylalkyl; $R_5$ is methyl; and $R_4$ is as defined in formula (I).

In another preferred embodiment, compounds of the present invention have formula (I) wherein $R_1$ is propyl; $R_2$ is fluorine; $R_3$ is $(NR_AR_B)$carbonylalkyl; $R_5$ is methyl; and $R_4$ is as defined in formula (I).

In another preferred embodiment, compounds of the present invention have formula (I) wherein $R_1$ is propyl; $R_2$ is alkyl; $R_3$ is $(NR_AR_B)$carbonylalkyl; $R_5$ is methyl; and $R_4$ is as defined in formula (I).

Another embodiment of the present invention relates to pharmaceutical compositions comprising a therapeutically effective amount of a compound of formula (I) in combination with a pharmaceutically acceptable carrier.

Another embodiment of the present invention relates to a method of treating epilepsy, migraine or a psychiatric disorder selected from Mood Disorders, Anxiety Disorders, Attention-Deficit and Disruptive Behavior Disorders, Behavioral Disturbances associated with dementia, Substance Abuse-related Disorders, Schizophrenia, Impulse Control Disorders, Personality Disorders and Behavioral Disturbances associated with autism in a mammal comprising administering to a mammal in need of such treatment a therapeutically effective amount of a compound of formula (I) in combination with a pharmaceutically acceptable carrier.

A preferred embodiment of the present invention relates to a method of treating epilepsy, migraine or a psychiatric disorder selected from Mood Disorders, Anxiety Disorders, Attention-Deficit and Disruptive Behavior Disorders, Behavioral Disturbances associated with dementia, Substance Abuse-related Disorders, Schizophrenia, Impulse Control Disorders, Personality Disorders and Behavioral Disturbances associated with autism in a mammal comprising administering to a mammal in need of such treatment a therapeutically effective amount of (2R)-2-propyl-4-hexynamide in combination with a pharmaceutically acceptable carrier.

Another preferred embodiment of the present invention relates to a method of treating epilepsy, migraine or a psychiatric disorder selected from Mood Disorders, Anxiety Disorders, Attention-Deficit and Disruptive Behavior Disorders, Behavioral Disturbances associated with dementia, Substance Abuse-related Disorders, Schizophrenia, Impulse Control Disorders, Personality Disorders and Behavioral Disturbances associated with autism in a mammal comprising administering to a mammal in need of such treatment a therapeutically effective amount of a compound selected from (2R)-N-(2-amino-2-oxoethyl)-2-propyl-4-hexynamide; (2R)-N-[(1S)-1-(aminocarbonyl)-2-methylpropyl]-2-propyl-4-hexynamide; (2R)-N-[(1S)-1-(aminocarbonyl)-3-methylbutyl]-2-propyl-4-hexynamide; (2R)-N-[(1S)-2-amino-1-methyl-2-oxoethyl]-2-propyl-4-hexynamide; and (2R)-N-[(1R)-2-amino-1-methyl-2-oxoethyl]-2-propyl-4-hexynamide in combination with a pharmaceutically acceptable carrier.

Definition of Terms

As used throughout this specification and the appended claims, the following terms have the following meanings:

The term "alkyl," as used herein, refers to a straight or branched chain hydrocarbon containing from 1 to 10 carbon atoms. Representative examples of alkyl include, but are not limited to, methyl, ethyl, propyl, butyl, pentyl, hexyl, 3-methylhexyl, 2,2-dimethylpentyl, 2,3-dimethylpentyl, heptyl, octyl, nonyl, and decyl.

The term "halo" or "halogen," as used herein, refers to —Cl, —Br, —I or —F.

The term "haloalkyl," as used herein, refers to at least one halogen, as defined herein, appended to the parent molecular moiety through an alkyl group, as defined herein. Representative examples of haloalkyl include, but are not limited to, trifluoromethyl, pentafluoroethyl, 3,3,3-trifluoropropyl, 2,2-difluoropropyl, 2,3-difluoropropyl, 2,2,3,3,3,-pentafluoropropyl and 2-chloro-3-fluoropentyl.

The term "carbonyl," as used herein, refers to a —C(O)— group.

The term "—$NR_AR_B$," as used herein, refers to two groups, $R_A$ and $R_B$, which are appended to the parent molecular moiety through a nitrogen atom. $R_A$ and $R_B$ are each independently selected from hydrogen and alkyl.

The term "($NR_AR_B$)carbonyl," as used herein, refers to a —$NR_aR_B$ group, as defined herein, appended to the parent molecular moiety through a carbonyl group, as defined herein.

The term "($NR_AR_B$)carbonylalkyl," as used herein, refers to a ($NR_AR_B$)carbonyl group, as defined herein, appended to the parent molecular moiety through an alkyl group, as defined herein. Representative examples of ($NR_AR_B$)carbonylalkyl include, but are not limited to, 2-amino-2-oxoethyl, (1S)-2-amino-1-methyl-2-oxoethyl, (1R)-2-amino-1-methyl-2-oxoethyl, (1S)-1-(aminocarbonyl)-2-methylpropyl, (1R)-1-(aminocarbonyl)-2-methylpropyl, (1S)-1-(aminocarbonyl)-3-methylbutyl, (1R)-1-(aminocarbonyl)-3-methylbutyl, and (1S,2R)4-amino-2-ethyl-1-isobutyl-4-oxobutyl.

Preferred compounds of formula (I) include, (2R)-N-(2-amino-2-oxoethyl)-2-propyl-4-hexynamide;

(2R)-N-[(1S)-1-(aminocarbonyl)-2-methylpropyl]-2-propyl-4-hexynamide;

(2R)-N-[(1S)-1-(aminocarbonyl)-3-methylbutyl]-2-propyl-4-hexynamide;

(2R)-N-[(1S)-2-amino-1-methyl-2-oxoethyl]-2-propyl-4-hexynamide; and (2R)-N-[(1R)-2-amino-1-methyl-2-oxoethyl]-2-propyl-4-hexynamide.

A most preferred compound is (2R)-2-propyl-4-hexynamide.

Abbreviations

Abbreviations which have been used in the descriptions of the schemes and the examples that follow are: DMF for N,N-dimethylformamide; DMSO for dimethylsulfoxide; HRMS for High Resolution Mass Spectroscopy; and LDA for lithium dilsopropylamine.

Preparation of Compounds of the Invention

The compounds and processes of the present invention will be better understood in connection with the following synthetic schemes and methods which illustrate a means by which the compounds of the invention can be prepared.

The compounds of this invention can be prepared by a variety of synthetic routes. Representative procedures are shown in Schemes 1–3.

Scheme 1

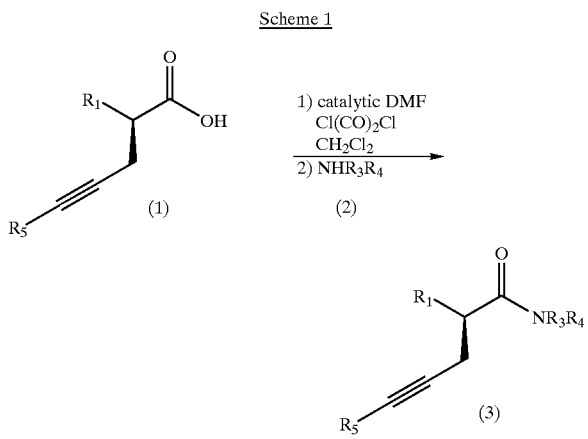

Alkynyl amides of general formula (3), wherein $R_1$, $R_3$, $R_4$ and $R_5$ are as defined in formula (I), may be prepared as described in Scheme 1. Alkynyl acids of general formula (1), prepared according to U.S. Pat. No. 5,786,380 hereby fully incorporated by reference, may be treated with oxalyl chloride and catalytic DMF in a solvent such as methylene chloride to provide crude acid chlorides. The crude acid chlorides may then be treated with an amine of general formula (2) in a solvent such as methylene chloride to provide alkynyl amides of general formula of general formula (3).

Scheme 2

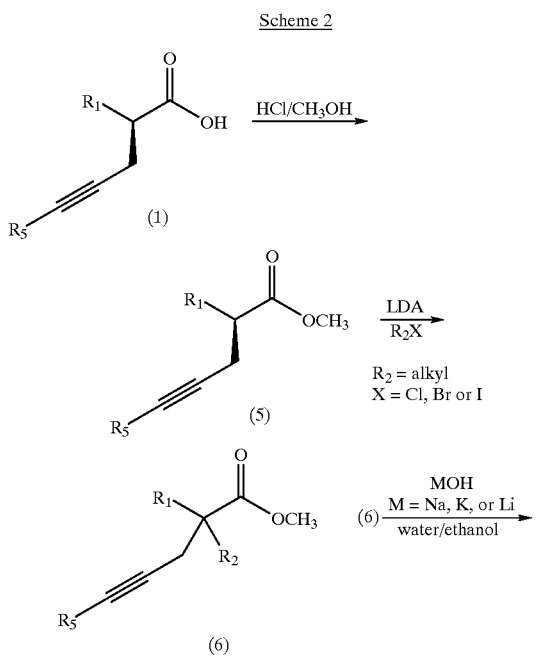

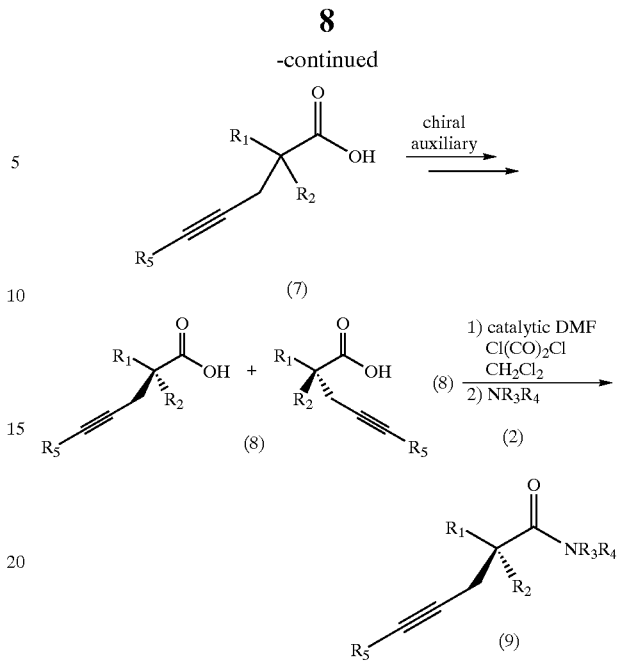

Alkynyl amides of general formula (9), wherein $R_1$, $R_3$, $R_4$ and $R_5$ are as defined in formula (I) and $R_2$ is alkyl, may be prepared as described in Scheme 2. Alkynyl acids of general formula (I) may be treated with HCl in methanol to provide alkynyl esters of general formula (5). Alkynyl esters of general formula (5) may be treated with lithium diisopropylamine and an alkyl halide to provide esters of general formula (6). Esters of general formula (6) may be treated with aqueous base such as potassium hydroxide in a solvent such as water/ethanol to provide acids of general formula (7). Acids of general formula (7) may be separated into individual enantiomers using chiral auxiliaries which is well known in the art such as the use of chiral oxazolidinones (Evans et al. J. Am. Chem. soc., (1982)104 1737–1739) to provide chiral acids of general formula (8). An example of separation of similar acids is described in U.S. Pat. No. 5,786,380. Chiral acids of general formula (8) may be processed as described in Scheme 1 to provide alkynyl amides of general formula (9).

Scheme 3

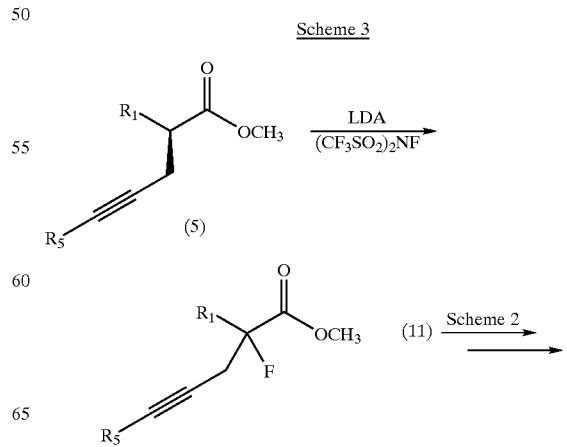

-continued

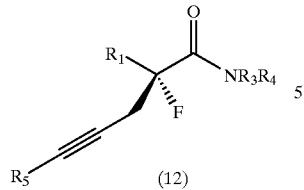

Alkynyl amides of general formula (12), wherein $R_1$, $R_3$, $R_4$ and $R_5$ are as defined in formula (1), may be prepared as described in Scheme 3. Esters of general formula (5) may be treated with lithium diisopropylamine and an electrophilic source of fluorine such as N-fluoro-N-[(trifluoromethyl) sulfonyl]trifluoromethanesulfonamide, other reagents known to be electrophilic sources of fluorine may be purchased commercially or prepared as described in (Chem. Rev., (1996) vol. 96 No.5; and Clark, J. H., Wails, D., Bastock, T. W., Aromatic Fluorination, CRC Press, 1996), to provide fluorinated ester of general formula (11). Fluorinated esters of general formula (11) may be processed as described in Scheme 2 to provide alkynyl amides of general formula (12).

The compounds and processes of the present invention will be better understood by reference to the following examples, which are intended as an illustration of and not a limitation upon the scope of the invention. Further, all citations herein are incorporated by reference.

EXAMPLE 1

(2R)-N-(2-amino-2-oxoethyl)-2-propyl-4-hexynamide (2R)-2-Propyl-4-hexynoic acid (2.0 g, 13 mmol, prepared according to U.S. Pat. No. 5,786,380) in dichloromethane (20 mL) was treated with 2 drops of N,N-dimethylformamide and freshly distilled oxalyl chloride (1.25 equivalents) at 0° C. The mixture was allowed to warm to ambient temperature. After stirring for 3 hours at ambient temperature, the solvents were removed under reduced pressure to provide crude acid chloride. The crude acid chloride was dissolved in dichloromethane (15 mL) and added dropwise to a solution of 2-aminoacetamide hydrochloride (14 mmol) and triethylamine (3.5 mL) in water at 0° C. The mixture was allowed to warm to ambient temperature. After stirring for 3 hours at ambient temperature, the mixture was cooled to about 5° C. and treated with 1N HCl until pH=2. The resulting white solid was collected by filtration, dried and recrystallized from ethyl acetate to provide the title compound (70% yield).

$^1$H NMR (300 MHz, DMSO-$d_6$) $\delta$8.1 (t, J=5.7 Hz, 1H), 7.0 (s, 2H), 3.6 (m, 2H), 2.4–2.1 (m, 3H), 1.7 (t, 2 Hz, 3H), 1.4 (m, 2H), 1.2 (m, 2H) 0.8 (t, J=7.5 Hz, 3H); MS (ESI+) m/z 211 (M+H)$^+$; HRMS: calculated 211.1447, found 211.1442.

EXAMPLE 2

(2R)-N-[(1S)-1-(aminocarbonyl)-2-methylpropyl]-2-propyl-4-hexynamide (2R)-2-Propyl-4-hexynoic acid and (2S)-2-amino-3-methylbutanamide were processed as described in Example 1.

$^1$H NMR (300 MHz, DMSO-$d_6$) $\delta$7.7 (d, J=9 Hz, 1H), 7.2 (s, 1H), 6.9 (s, 1H), 4.1 (m, 1H), 3.0 (m, 1H), 2.5 (m, 1H), 2.1 (m, 2H), 1.9 (m, 1H), 1.6 (s, 3H), 1.3 (m, 2H), 1.2 (m, 2H), 0.8 (m, 9H); MS (CI) m/z 253 (M+H)$^+$.

EXAMPLE 3

(2R)-N-[(1S)-1-(aminocarbonyl)-3-methylbutyl]-2-propyl-4-hexynamide (2R)-2-Propyl-4-hexynoic acid and (2S)-2-amino-4-methylpentanamide were processed as described in Example 1.

$^1$H NMR (300 MHz, DMSO-$d_6$) $\delta$7.9 (d, J=9 Hz, 1H), 7.1 (s, 1H), 6.9 (s, 1H), 4.2 (m, 1), 3.0 (m, 1H), 2.4 (m, 1H), 2.1 (m, 2 H), 1.6 (s, 3H), 1.6–1.1 (m, 6H), 0.8 (m, 9H); MS (CI) m/z 253 (M+H)$^+$.

EXAMPLE 4

(2R)-N-[(1S)-2-amino-1-methyl-2-oxoethyl]-2-propyl-4-hexynamide (2R)-2-Propyl-4-hexynoic acid and (2S)-2-aminopropanamide were processed as described in Example 1.

$^1$H NMR (300 MHz, DMSO-$d_6$) $\delta$7.9 (d, J=8 Hz, 1H), 7.3 (s, 1H), 6.9 (s, 1H), 4.2 (m, 1H), 3.0 (m, 1H), 2.4 (m, 1H), 2.2 (m, 2H), 1.7 (m, 1H), 1.4 (s, 3H), 1.2 (m, 2H), 0.8 (t, J=7 Hz, 3H); MS (CI) m/z 225 (M+H)$^+$.

EXAMPLE 5

(2R)-N-[(1R)-2-amino-1-methyl-2-oxoethyl]-2-propyl-4-hexynamide (2R)-2-Propyl-4-hexynoic acid and (2R)-2-aminopropanamide were processed as described in Example 1.

$^1$H NMR (300 MHz, DMSO-$d_6$) $\delta$8.0 (d, J=8 Hz, 1H), 7.0 (s, 2H), 4.2 (m, 1H), 3.1 (q, J=6 Hz, 1H), 2.4 (m, 1H), 2.2 (m, 2H), 1.7 (m, 1H), 1.4 (s, 3H), 1.2 (m, 2H), 0.8 (J=7 Hz, 3H); MS (CI) m/z 225 (M+H)$^+$.

EXAMPLE 6

(2R)-2-propyl-4-hexynamide (2R)-2-Propyl-4-hexynoic acid (1.5 g 10 mmol) in dichloromethane (15 mL) was treated with 2 drops of N,N-dimethylformamide and freshly distilled oxalyl chloride (1.25 equivalents) at 0° C. The mixture was allowed to warm to ambient temperature. After stirring for 3 hours at ambient temperature, the solvents were removed under reduced pressure to provide the crude acid. The acid chloride was dissolved in dichloromethane (15 mL) and ammonia gas was bubbled through the mixture at 0° C. for 30 minutes. The mixture was allowed to warm to ambient temperature and ammonia gas was bubbled through the mixture an additional 20 minutes. The mixture was treated with water (20 mL) and the resulting white solid collected by filtration, dried and recrystallized from ethyl acetate to provide the title compound (75% yield).

$^1$H NMR (300 MHz, DMSO-$d_6$) $\delta$7.3 (s, 1H), 6.8 (s, 1H), 2.2 (m, 2H), 2.1 (m, 1H), 1.7 (s, 3H), 1.4(m, 2H), 1.2(m, 2H), 0.8 (t, J=7 Hz, 3H); MS (CI) m/z 154 (M+H)$^+$.

Determination of Anticonvulsant Effect

The anticonvulsant effect of a representative number of compounds of the present invention were determined using the procedure described hereinafter.

Male CD1 mice (Charles River, Portage, Mich.) weighing 25–35 g were used and during the experiment the mice were housed individually in clear polycarbonate cages for observation. For each experiment, ten mice were each pretreated intra-peritoneally with a compound of the present invention (1400 μmol/kg) prior to pentylenetetrazole (PTZ) (Sigma, St. Louis, Mo.) injection. Seizures were induced by the subcutaneous injection of PTZ (85 mg/kg) just below the nape of the neck. The animals were observed for 15 minutes and time to seizure was noted. The data in Table 1 represents the average time for PTZ induced seizure. Also noted were the number of mice out of ten that did not seize within the 15 minute period following PTZ injection. This data is shown in Table 2. Control animals were not pretreated with a compound of the present invention but were injected with PTZ (85 mg/kg) subcutaneously.

TABLE 1

Latency to PTZ Induced Seizures in Mice

| Example Number | Time to Seizure (seconds) |
|---|---|
| control | 240 |
| 1 | 675 |
| 2 | 305 |
| 3 | 575 |
| 4 | 610 |
| 5 | 525 |
| 6 | No Seizures |

TABLE 2

Mice Protected Against PTZ Induced Seizures

| Example Number | Number of Mice Protected |
|---|---|
| control | 0 |
| 1 | 5 |
| 2 | 1 |
| 3 | 4 |
| 4 | 6 |
| 5 | 2 |
| 6 | 10 |

The data in Tables 1 and 2 illustrate the anticonvulsant effect of compounds of the present invention in mammals.

Maximum Electrical Shock Method (MES)

Male CD1 mice (Charles River) weighing from 25–35 g were used. Mice were pretreated orally with compounds of the present invention prior to electrical stimulation. Mice were challenge by pulsed electrical stimulation (50 mA, 0.4 s duration, pulse width 0.5 ms, 60 pulses/sec) via corneal electrodes to induce seizure. The stimulation was delivered with an ECT Unit (Ugo Basile #7801). The electrodes of the unit were coated with electrocardiogram electrolyte (Signa Creme, Parker Labs #1708) to ensure good contact with the corneas. Mice were observed post-stimulation for the onset of seizures and death. Mice were considered to have had a seizure only if there was an extended extension (>90° from plane of body) of the hind legs. Mice were assigned scores of either "positive" or "negative." A positive score indicates that seizure occurred; a negative score indicated that seizure did not occur. Animals which gave a positive seizure response were observed an additional 30 seconds for death. Those that did not seize were considered to be protected. The percent protection from seizures was calculated by dividing the number of protected mice by the total number of mice for the group. The percentage of mice protected from electrical shock induced seizures at doses of 600, 1200, 1800 and 2400 μmole/kg is illustrated in Table 3 for Example 1 and Example 6. The corresponding acid, (2R)-2-propyl-4-hexynoic acid, was also tested for comparison.

TABLE 3

Percentage of Mice Protected Against Electrical Shock Induced Seizures

| | Dose (μmole/kg) | | | |
|---|---|---|---|---|
| | 600 | 1200 | 1800 | 2400 |
| Example 1 | 0% | 70% | 90% | 100% |
| Example 6 | 0% | 20% | 90% | NT |
| (2R)-2-propyl-4-hexynoic acid | 0% | 0% | 0% | 20% |

NT in Table 3 means Not Tested.

The data in Table 3 illustrates the ability of alkynyl amides of the present invention to protect mice from electrical shock induced seizures. Alkynyl amides of the present invention unexpectedly protect a significantly higher percentage of mice when compared to the corresponding acid, (2R)-2-propyl-4-hexynoic acid.

The compounds of the present invention, including but not limited to those specified in the examples, possess an anticonvulsant effect as demonstrated by the data illustrated in Tables 1–3. As anticonvulsants, the compounds of the present invention may be useful for the treatment of a variety of disorder such as seizures, epilepsy, migraine, psychiatric disorders, neuropathic pain and restlessness syndrome.

Additionally, compounds of the present invention, including but not limited to those specified in the examples, may be useful for providing neuroprotection.

The ability of the compounds of the invention, including but not limited to those specified in the examples, to treat epilepsy may be demonstrated according to the methods described in (Loscher W., ed. Valproate, Basel Switzerland: Birkhauser Verlag, 1999; and Cereghino et al., "Introduction," in Antiepileptic Drugs, 4$^{th}$ ed., pages 1–11, Raven Press, 1995).

The ability of the compounds of the invention, including but not limited to those specified in the examples, to treat different types of migraine such as classical migraine and common migraine may be demonstrated according to the methods described in (Loscher W., ed. Valproate, Basel Switzerland: Birkhauser Verlag, 1999; Hering and Kuritzky, Cephalalgia, 12, 1992, 81–84; Hering and Kuritzky, Cephalalgia, 9, 1989, 195–198; and Mathew and Sabiha, Headache, 31, 1991, 71–74).

The ability of the compounds of the invention, including but not limited to those specified in the examples, to treat psychiatric disorders such as Mood Disorders, Anxiety Disorders, Attention-Deficit and Disruptive Behavior Disorders, Behavioral Disturbances associated with dementia, Substance Abuse-related Disorders, Schizophrenia, Impulse Control Disorders, Personality Disorders and Behavioral Disturbances associated with autism may be demonstrated according to the methods described in (Loscher W., ed. Valproate, Basel Switzerland: Birkhauser Verlag (1999); Post R. M., In Tasman A., Goldfinger, S. M., Kaufmann, C. A., eds. Review of psychiatry, volume 9, Washington D.C.: American Psychiatric Press, (1990) 170–202; Jensen R., Brinck T., Olesen J., Neurology 44 (1994) 647; Bernasconi et al., in Anticonvulsants In Affective Disorders, pages 14–32, Excerpta Medica, 1984; Lloyd and Morselli, in Psychopharmacology: The Third Generation of Progress, Raven Press, 1987).

The ability of the compounds of the invention, including but not limited to those specified in the examples, to provide neuroprotection may be demonstrated according to the methods described in (Chen G., et al, Journal of Neurochemistry, 1999, 879–882; and Lyden, Chapter 10 in "Neuroprotective Agents and Cerebral Ischaemia", IRN 40, Academic Press Limited, 1997.

The ability of the compounds of the invention, including but not limited to those specified in the examples, to treat neuropathic pain may be demonstrated according to the methods described in (Lloyd and Morselli, in Psychopharmacology: The Third Generation of Progress, Raven Press, 1987; and Swendlow, J. Clin. Neuropharmacol., 7, 1984, 51–82).

The ability of the compounds of the invention, including but not limited to those specified in the examples, to treat Restlessness Syndrome may be demonstrated according to the methods described in (O'Keefe, Arch. Intern. Med. 156, 1996, 24348; Danek et al., in Neurological Disorders: Course and Treatment, pages 819–23, Academic Press, 1996; and Mellick and Mellick, Neurology 45(suppl), 1995, 285–86.

Compounds of the present invention may exist as stereoisomers wherein, asymmetric or chiral centers are present. These stereoisomers are "R" or "S" depending on the configuration of substituents around the chiral carbon atom. The terms "R" and "S" used herein are configurations as defined in IUPAC 1974 Recommendations for Section E, Fundamental Stereochemistry, Pure Appl. Chem., 1976, 45: 13–30. In particular, the stereochemistry at the 2-position of the 4-hexynamides, as shown in formula (I), may be only (R) when $R_2$ is hydrogen or alkyl and may be only (S) when $R_2$ is fluorine. Additionally, when $R_3$ is $(NR_AR_B)$carbonylalkyl, the alkyl portion may contain one or two chiral centers. The one or two chiral centers contained within the alkyl portion of $(NR_AR_B)$carbonylalkyl may be independently either (R) or (S), unless specifically noted otherwise. However, the present invention does contemplate various stereoisomers and mixtures thereof and are specifically included within the scope of this invention. Stereoisomers include enantiomers and diastereomers, and mixtures of enantiomers or diastereomers. Individual stereoisomers of compounds of the present invention may be prepared synthetically from commercially available starting materials which contain asymmetric or chiral centers or by preparation of racemic mixtures followed by resolution well-known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary or (2) direct separation of the mixture of optical enantiomers on chiral chromatographic columns or (3) formation of a salt with a chiral amine and separating the enantiomers via fractional crystallization.

The present invention contemplates prodrugs that are transformed by in vivo biotransformation into compounds of formula (I).

The term "prodrug," as used herein, represents those prodrugs of the compounds of the present invention which are, within the scope of sound medical judgement, suitable for use in contact with the tissues of humans and lower animals without undue toxicity, irritation, allergic response, and the like, commensurate with a reasonable benefit/risk ratio, and effective for their intended use. Prodrugs of the present invention may be rapidly transformed in vivo to compounds of formula (I), for example, by hydrolysis in blood. A thorough discussion is provided in T. Higuchi and V. Stella, Pro-drugs as Novel Delivery Systems, V. 14 of the A.C.S. Symposium Series, and in Edward B. Roche, ed., Bioreversible Carriers in Drug Design, American Pharmaceutical Association and Pergamon Press, 1987.

The term "pharmaceutically acceptable carrier," as used herein, means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil, glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The present invention provides pharmaceutical compositions which comprise compounds of the present invention formulated together with one or more non-toxic pharmaceutically acceptable carriers. The pharmaceutical compositions can be formulated for oral administration in solid or liquid form, for parenteral injection or for rectal administration.

Further included within the scope of the present invention are pharmaceutical compositions comprising one or more of the compounds of formula (I) prepared and formulated in combination with one or more non-toxic pharmaceutically acceptable compositions. The pharmaceutical compositions can be formulated for oral administration in solid or liquid form, for parenteral injection or for rectal administration.

The pharmaceutical compositions of this invention can be administered to humans and other mammals orally, rectally, parenterally, intracisternally, intravaginally, intraperitoneally, topically (as by powders, ointments or drops), bucally or as an oral or nasal spray. The term "parenterally," as used herein, refers to modes of administration which include intravenous, intramuscular, intraperitoneal, intrastemal, subcutaneous, intraarticular injection and infusion.

Pharmaceutical compositions of this invention for parenteral injection comprise pharmaceutically acceptable sterile aqueous or nonaqueous solutions, dispersions, suspensions or emulsions and sterile powders for reconstitution into sterile injectable solutions or dispersions. Examples of suitable aqueous and nonaqueous carriers, diluents, solvents or vehicles include water, ethanol, polyols (propylene glycol, polyethylene glycol, glycerol, and the like), suitable mixtures thereof, vegetable oils (such as olive oil) and injectable organic esters such as ethyl oleate. Proper fluidity may be maintained, for example, by the use of a coating such as lecithin, by the maintenance of the required particle size in the case of dispersions, and by the use of surfactants.

These compositions may also contain adjuvants such as preservative agents, wetting agents, emulsifying agents, and dispersing agents. Prevention of the action of microorganisms may be ensured by various antibacterial and antifungal agents, for example, parabens, chlorobutanol, phenol, sorbic acid, and the like. It may also be desirable to include isotonic agents, for example, sugars, sodium chloride and the like. Prolonged absorption of the injectable pharmaceutical form may be brought about by the use of agents delaying absorption, for example, aluminum monostearate and gelatin.

In some cases, in order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Suspensions, in addition to the active compounds, may contain suspending agents, as, for example, ethoxylated isostearyl alcohols, polyoxyethylene sorbitol and sorbitan esters, microcrystalline cellulose, aluminum metahydroxide, bentonite, agar-agar, tragacanth, and mixtures thereof If desired, and for more effective distribution, the compounds of the present invention can be incorporated into slow-release or targeted-delivery systems such as polymer matrices, liposomes, and microspheres. They may be sterilized, for example, by filtration through a bacteria-retaining filter or by incorporation of sterilizing agents in the form of sterile solid compositions, which may be dissolved in sterile water or some other sterile injectable medium immediately before use.

The active compounds can also be in micro-encapsulated form, if appropriate, with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound can be admixed with at least one inert diluent such as sucrose, lactose, or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of such composition that they release the active ingredient(s) only, or preferentially, in a certain part of the intestinal tract in a delayed manner. Examples of embedding compositions which can be used include polymeric substances and waxes.

Injectable depot forms are made by forming microencapsulated matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides) Depot injectable formulations are also prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic, parenterally acceptable diluent or solvent such as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid; b) binders such as carboxymethylcellulose, alginates, gelatin, polyvinylpyrrolidinone, sucrose, and acacia; c) humectants such as glycerol; d) disintegrating agents such as agar-agar, calcium carbonate, potato or tapioca starch, alginic acid, certain silicates, and sodium carbonate; e) solution retarding agents such as paraffin); f) absorption accelerators such as quatemary ammonium compounds; g) wetting agents such as cetyl alcohol and glycerol monostearate;) absorbents such as kaolin and bentonite clay; and i) lubricants such as talc, calcium stearate, magnesium stearate, solid polyethylene glycols, sodium lauryl sulfate, and mixtures thereof In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract in a delayed manner. Examples of embedding compositions which can be used include polymeric substances and waxes.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Compounds of the present invention may also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes may be used. The present compositions in liposome form may contain, in addition to the compounds of the present invention, stabilizers, preservatives, excipients, and the like. The preferred lipids are the natural and synthetic phospholipids and phosphatidylcholines (lecithins) used separately or together.

Methods to form liposomes are known in the art. See, for example, Prescott, Ed., Methods in Cell Biology, Volume XIV, Academic Press, New York, N.Y., (1976), p 33 et seq.

The term "pharmaceutically acceptable cation," as used herein, refers to a positively-charged inorganic or organic ion that is generally considered suitable for human consumption. Examples of pharmaceutically acceptable cations are hydrogen, alkali metal (lithium, sodium and potassium), magnesium, calcium, ferrous, ferric, ammonium, alkylammonium, dialkylammonium, trialkylammonium, tetraalkylammonium, diethanolammmonium, and choline. Cations may be interchanged by methods known in the art, such as ion exchange.

The term "pharmaceutically acceptable salt," as used herein, refers to salts that are well known in the art. For example, S. M Berge et al. describe pharmaceutically acceptable salts in detail in (J. Pharmaceutical Sciences, 66:1–19 (1977)). Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid, or malonic acid or by using other methods used in the art such as ion exchange. Other pharmaceutically acceptable salts include nitrate, bisulfate, borate, formate, butyrate, valerate, 3-phenylpropionate, camphorate, adipate, benzoate, oleate, palmitate, stearate, laurate, lactate, fumarate, ascorbate, aspartate, nicotinate, p-toluenesulfonate, camphorsulfonate, methanesulfonate, 2-hydroxyethanesulfonate, gluconate, glucoheptonate, lactobionate, glycerophosphate, pectinate, lauryl sulfate, and the like, metal salts such as sodium, potassium, magnesium or calcium salts or amino salts such as ammonium, triethylamine salts, and the like, all of which may be prepared according to conventional methods.

Dosage forms for topical administration of a compound of this invention include powders, sprays, ointments and inhalants. The active compound is mixed under sterile conditions with a pharmaceutically acceptable carrier and any needed preservatives, buffers or propellants which can be required. Opthalmic formulations, eye ointments, powders and solutions are also contemplated as being within the scope of this invention.

Actual dosage levels of active ingredients in the pharmaceutical compositions of this invention can be varied so as to obtain an amount of the active compound(s) which is effective to achieve the desired therapeutic response for a particular patient, compositions and mode of administration. The selected dosage level will depend upon the activity of the particular compound, the route of administration, the severity of the condition being treated and the condition and prior medical history of the patient being treated. However, it is within the skill of the art to start doses of the compound at levels lower than required for to achieve the desired therapeutic effect and to gradually increase the dosage until the desired effect is achieved.

Aqueous liquid compositions of the present invention may be particularly useful for the treatment and prevention of seizures, in particular, seizures associated with epilepsy.

When used in the above or other treatments, a therapeutically effective amount of one of the compounds of the present invention can be employed in pure form or, where such forms exist, in pharmaceutically acceptable salt form. Alternatively, the compound can be administered as a pharmaceutical composition containing the compound of interest in combination with one or more pharmaceutically acceptable excipients. The phrase "therapeutically effective amount" of the compound of the invention means a sufficient amount of the compound to treat disorders, at a reasonable benefit/risk ratio applicable to any medical treatment. It will be understood, however, that the total daily usage of the compounds and compositions of the present invention will be decided by the attending physician within the scope of sound medical judgement. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts. For example, it is well within the skill of the art to start doses of the compound at levels lower than required to achieve the desired therapeutic effect and to gradually increase the dosage until the desired effect is achieved.

The total daily dose of the compounds of this invention administered to a human or lower animal may range from about 0.003 to about 30 mg/kg/day. For purposes of oral administration, more preferable doses can be in the range of from about 0.01 to about 10 mg/kg/day. If desired, the effective daily dose can be divided into multiple doses for purposes of administration; consequently, single dose compositions may contain such amounts or submultiples thereof to make up the daily dose.

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations and/or methods of use of the invention, may be made without departing from the spirit and scope thereof.

What is claimed is:

1. A compound of formula (I)

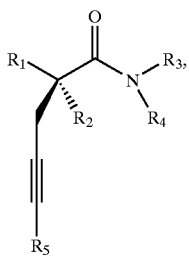

wherein
- $R_1$ is selected from the group consisting of alkyl and haloalkyl;
- $R_2$ is selected from the group consisting of hydrogen, alkyl and fluorine;
- $R_3$ is $(NR_AR_B)$ carbonylalkyl wherein $R_A$ and $R_B$ are each independently selected from the group consisting of hydrogen and alkyl;
- $R_4$ is selected from the group consisting of hydrogen and alkyl; and
- $R_5$ is selected from the group consisting of hydrogen and alkyl.

2. A compound according to claim 1 wherein
- $R_1$ is alkyl wherein said alkyl is propyl; and
- $R_5$ is alkyl wherein said alkyl is methyl.

3. A compound according to claim 2 wherein $R_3$ is $(NR_AR_B)$carbonylalkyl.

4. A compound according to claim 3 selected from the group consisting of (2R)-N-(2-amino-2-oxoethyl)-2-propyl-4-hexynamide;
- (2R)-N-[(1S)-1-(aminocarbonyl)-2-methylpropyl]-2-propyl-4-hexynamide;
- (2R)-N-[(1S)-1-(aminocarbonyl)-3-methylbutyl]-2-propyl-4-hexynamide;
- (2R)-N-[(1S)-2-amino-1-methyl-2-oxoethyl]-2-propyl-4-hexynamide; and
- (2R)-N-[(1R)-2-amino-1-methyl-2-oxoethyl]-2-propyl-4-hexynamide.

5. A compound according to claim 2 wherein
- $R_3$ is $(NR_AR_B)$carbonylalkyl; and
- $R_2$ is fluorine.

6. A compound according to claim 2 wherein
- $R_3$ is $(NR_AR_B)$carbonylalkyl; and
- $R_2$ is alkyl.

7. A method of treating seizures in a mammal comprising administering to said mammal in need of such treatment a therapeutically effective amount of a compound of formula (I), as according to claim 1.

8. A method of treating epilepsy in a mammal comprising administering to said mammal in need of such treatment a therapeutically effective amount of a compound of formula (I), as according to claim 1.

9. A method of treating migraine in a mammal comprising administering to said mammal in need of such treatment a therapeutically effective amount of a compound of formula (I), as according to claim 1.

10. A method of treating psychiatric disorders selected from the group consisting of Mood Disorders, Anxiety Disorders, Attention-Deficit and Disruptive Behavior Disorders, Behavioral Disturbances associated with dementia, Substance Abuse-related Disorders, Schizophrenia, Impulse Control Disorders, Personality Disorders and Behavioral Disturbances associated with autism in a mammal comprising administering to said mammal in need of such treatment a therapeutically effective amount of a compound of formula (I), as according to claim 1.

11. A method of treating neuropathic pain in a mammal comprising administering to said mammal in need of such treatment a therapeutically effective amount of a compound of formula (I), as according to claim 1.

12. A method of treating restlessness syndrome in a mammal comprising administering to said mammal in need of such treatment a therapeutically effective amount of a compound of formula (I), as according to claim 1.

13. A method of providing neuroprotection to a mammal suffering from a cerebral insult, comprising administering to said mammal a therapeutically effective amount of a compound of formula (I), as according to claim 1.

14. The method of claim 7, wherein the compound is (2R)-2-propyl-4-hexynamide.

15. The method of claim 8, wherein the compound is (2R)-2-propyl-4-hexynamide.

16. The method of claim 9, wherein the compound is (2R)-2-propyl-4-hexynamide.

17. The method of claim 10, wherein the compound is (2R)-2-propyl-4-hexynamide.

18. The method of claim 11, wherein the compound is (2R)-2-propyl-4-hexynamide.

19. The method of claim 12, wherein the compound is (2R)-2-propyl-4-hexynamide.

20. The method of claim 13, wherein the compound is (2R)-2-propyl-4-hexynamide.

21. The method of claim 7, wherein the compound is selected from the group consisting of
- (2R)-N-(2-amino-2-oxoethyl)-2-propyl-4-hexynamide;
- (2R)-N-[(1S)-1-(aminocarbonyl)-2-methylpropyl]-2-propyl-4-hexynamide;
- (2R)-N-[(1S)-1-(aminocarbonyl)-3-methylbutyl]-2-propyl-4-hexynamide;
- (2R)-N-[(1S)-2-amino-1-methyl-2-oxoethyl]-2-propyl-4-hexynamide; and
- (2R)-N-[(1R)-2-amino-1-methyl-2-oxoethyl]-2-propyl-4-hexynamide.

22. The method of claim 8, wherein the compound is selected from the group consisting of
- (2R)-N-(2-amino-2-oxoethyl)-2-propyl-4-hexynamide;
- (2R)-N-[(1S)-1-(aminocarbonyl)-2-methylpropyl]-2-propyl-4-hexynamide;
- (2R)-N-[(1S)-1-(aminocarbonyl)-3-methylbutyl]-2-propyl-4-hexynamide;
- (2R)-N-[(1S)-2-amino-1-methyl-2-oxoethyl]-2-propyl-4-hexynamide; and
- (2R)-N-[(1R)-2-amino-1-methyl-2-oxoethyl]-2-propyl-4-hexynamide.

23. The method of claim 9, wherein the compound is selected from the group consisting of
- (2R)-N-(2-amino-2-oxoethyl)-2-propyl-4-hexynamide;
- (2R)-N-[(1S)-1-(aminocarbonyl)-2-methylpropyl]-2-propyl-4-hexynamide;
- (2R)-N-[(1S)-1-(aminocarbonyl)-3-methylbutyl]-2-propyl-4-hexynamide;
- (2R)-N-[(1S)-2-amino-1-methyl-2-oxoethyl]-2-propyl-4-hexynamide; and (2R)-N-[(1R)-2-amino-1-methyl-2-oxoethyl]-2-propyl-4-hexynamide.

24. The method of claim 10, wherein the compound is selected from the group consisting of (2R)-N-(2-amino-2-oxoethyl)-2-propyl-4-hexynamide;

(2R)-N-[(1S)-1-(aminocarbonyl)-2-methylpropyl]-2-propyl-4-hexynamide;

(2R)-N-[(1S)-1-(aminocarbonyl)-3-methylbutyl]-2-propyl-4-hexynamide;

(2R)-N-[(1S)-2-amino-1-methyl-2-oxoethyl]-2-propyl-4-hexynamide; and (2R)-N-[(1R)-2-amino-1-methyl-2-oxoethyl]-2-propyl-4-hexynamide.

25. The method of claim 11, wherein the compound is selected from the group consisting of (2R)-N-(2-amino-2-oxoethyl)-2-propyl-4-hexynamide;

(2R)-N-[(1S)-1-(aminocarbonyl)-2-methylpropyl]-2-propyl-4-hexynamide;

(2R)-N-[(1S)-1-(aminocarbonyl)-3-methylbutyl]-2-propyl-4-hexynamide;

(2R)-N-[(1S)-2-amino-1-methyl-2-oxoethyl]-2-propyl-4-hexynamide; and (2R)-N-[(1R)-2-amino-1-methyl-2-oxoethyl]-2-propyl-4-hexynamide.

26. The method of claim 12, wherein the compound is selected from the group consisting of (2R)-N-(2-amino-2-oxoethyl)-2-propyl-4-hexynamide;

(2R)-N-[(1S)-1-(aminocarbonyl)-2-methylpropyl]-2-propyl-4-hexynamide;

(2R)-N-[(1S)-1-(aminocarbonyl)-3-methylbutyl]-2-propyl-4-hexynamide;

(2R)-N-[(1S)-2-amino-1-methyl-2-oxoethyl]-2-propyl-4-hexynamide; and (2R)-N-[(1R)-2-amino-1-methyl-2-oxoethyl]-2-propyl-4-hexynamide.

27. The method of claim 13, wherein said compound is selected from the group consisting of (2R)-N-(2-amino-2-oxoethyl)-2-propyl-4-hexynamide;

(2R)-N-[(1S)-1-(aminocarbonyl)-2-methylpropyl]-2-propyl-4-hexynamide;

(2R)-N-[(1S)-1-(aminocarbonyl)-3-methylbutyl]-2-propyl-4-hexynamide;

(2R)-N-[(1S)-2-amino-1-methyl-2-oxoethyl]-2-propyl-4-hexynamide; and (2R)-N-[(1R)-2-amino-1-methyl-2-oxoethyl]-2-propyl-4-hexynamide.

28. A pharmaceutical composition comprising a therapeutically effective amount of a compound of claim 1 in combination with a pharmaceutically acceptable carrier.

* * * * *